(12) United States Patent
Takeuchi et al.

(10) Patent No.: US 11,420,805 B2
(45) Date of Patent: Aug. 23, 2022

(54) FRAGILE OBJECT HOLDING DEVICE PROVIDED WITH PROTECTING MECHANISM

(71) Applicant: TERUMO KABUSHIKI KAISHA, Tokyo (JP)

(72) Inventors: Ryohei Takeuchi, Kanagawa (JP); Akihiro Takahashi, Kanagawa (JP); Yosuke Kuruma, Kanagawa (JP); Toshikazu Takeuchi, Kanagawa (JP); Kenta Mizumoto, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 2 days.

(21) Appl. No.: 16/903,860

(22) Filed: Jun. 17, 2020

(65) Prior Publication Data

US 2020/0307889 A1    Oct. 1, 2020

Related U.S. Application Data

(63) Continuation of application No. PCT/JP2018/046483, filed on Dec. 18, 2018.

(30) Foreign Application Priority Data

Dec. 18, 2017    (JP) .............................. JP2017-241716

(51) Int. Cl.
*B65D 81/05*    (2006.01)
*A01N 1/02*    (2006.01)
(Continued)

(52) U.S. Cl.
CPC ......... *B65D 81/052* (2013.01); *A01N 1/0273* (2013.01); *B65D 81/22* (2013.01); *B65D 85/50* (2013.01); *B65D 2581/05* (2013.01)

(58) Field of Classification Search
CPC ...... A01N 1/02; A01N 1/0273; A01N 1/2096; B65D 53/02; B65D 81/05; B65D 81/052;
(Continued)

(56) References Cited

U.S. PATENT DOCUMENTS 2,943,387 A * 7/1960 Dawson .............. F16L 13/0263
228/226
4,415,076 A * 11/1983 Campbell ............ A45C 11/005
134/137

(Continued)

FOREIGN PATENT DOCUMENTS

JP      H0630760 A      2/1994
JP      2009089715 A    4/2009
(Continued)

OTHER PUBLICATIONS

An English Translation of the International Search Report (Form PCT/ISA/210) and the Written Opinion of the International Searching Authority (Form PCT/ISA/237) dated Mar. 26, 2019, by the Japanese Patent Office in corresponding International Application No. PCT/JP2018/046483. (11 pages).

*Primary Examiner* — Bryon P Gehman
(74) *Attorney, Agent, or Firm* — Buchanan Ingersoll & Rooney PC (57) ABSTRACT

A device for stably maintaining the shape of a fragile object in a liquid includes a container for accommodating the fragile object, a lid member for sealing the container, and a protecting member. The device is configured to form a liquid-tight space by covering a liquid surface in the container which accommodates the fragile object and the liquid with the protecting member and further covering the protecting member and an open portion of the container with the lid member.

21 Claims, 3 Drawing Sheets

(51) Int. Cl.
*B65D 81/22* (2006.01)
*B65D 85/50* (2006.01)

(58) Field of Classification Search
CPC ........ B65D 81/22; B65D 81/24; B65D 85/50;
B65D 2581/05
USPC .......................................... 206/205–212, 521
See application file for complete search history.

(56) References Cited

U.S. PATENT DOCUMENTS

| | | | |
|---|---|---|---|
| 7,784,608 B2* | 8/2010 | Tokarski | A45C 11/005 206/5.1 |
| 8,703,074 B2* | 4/2014 | Nozaki | A01N 1/0263 422/559 |
| 8,999,703 B2* | 4/2015 | Welch | A01N 1/0273 435/304.1 |
| 9,521,840 B2* | 12/2016 | Kawasaki | C12M 45/22 |
| 2015/0231628 A1* | 8/2015 | Nozaki | B65B 3/04 422/547 |

FOREIGN PATENT DOCUMENTS

| | | |
|---|---|---|
| JP | 2012130311 A | 7/2012 |
| JP | 2015043751 A | 3/2015 |
| WO | 2013094370 A1 | 6/2013 |
| WO | 2014041593 A1 | 3/2014 |
| WO | 2016208018 A1 | 12/2016 |

\* cited by examiner

FRAGILE OBJECT HOLDING DEVICE PROVIDED WITH PROTECTING MECHANISM

CROSS-REFERENCES TO RELATED APPLICATIONS

This application is a continuation of International Patent Application No. PCT/JP2018/046483 filed on Dec. 18, 2018 which claims priority to Japanese Patent Application No. 2017-241716 filed on Dec. 18, 2017, the entire content of both of which is incorporated herein by reference.

FIELD OF THE INVENTION

The present invention generally relates to a fragile object holding device provided with a protecting mechanism.

BACKGROUND DISCUSSION

In recent years, new regenerative medicine has been developed as a solution for severe heart failure treatment. As an example, a technique has been attempted involving applying a sheet-like cell culture produced using a temperature-responsive culture dish, to which tissue engineering is applied, to a heart surface in a case of severe myocardial infarction. The technique using the sheet-like cell culture enables safe transplant of a large number of cells in a wide range, and is particularly useful in treatment such as myocardial infarction (chronic heart failure associated with myocardial infarction), dilated cardiomyopathy, ischemic cardiomyopathy, and heart disease (for example, heart failure, particularly chronic heart failure) associated with contractile dysfunction (for example, left ventricular systolic dysfunction).

In order to use such a sheet-like cell culture in clinical application, for example, it is necessary to accommodate the produced sheet-like cell culture together with a preservation solution in a container and transport the container to an intensive care unit where transplant is performed. However, since the sheet-like cell culture has low absolute physical strength and the sheet-like cell culture wrinkles, cracks, and is damaged due to vibration generated when transporting the container, highly sophisticated technology is required in this transporting operation, and it is necessary to take great care.

Various methods and containers have been developed to meet such needs. For example, a package for transporting a cultured cell sheet is disclosed in Japanese Patent Application Publication No. 2009-89715. As liquid-tightness is caused by exhausting air together with a small amount of a liquid culture medium when sealing with a lid, bubbles do not move in the liquid culture medium during transportation. Thus, such a package can prevent the shift and breakage of the cultured cell sheet.

A preservation transport container for a membrane-like tissue disclosed in Japanese Patent Application Publication No. 2012-130311 causes a preservation solution not to ripple or flow by filling a containing unit with the preservation solution to a degree that a gas layer is not formed and causing liquid-tightness, and consequently can prevent damage to the membrane-like tissue without transmitting vibration to the membrane-like tissue.

SUMMARY

As described above, a container for safely transporting a fragile cell sheet has been developed. In addition, research on such a container has been conducted such that the inside of the container is made liquid-tight and movement of bubbles does not occur.

However, highly sophisticated technology is required to completely remove bubbles from the inside of the container and achieve a liquid-tight state. In addition, since a strong force is necessary to remove a lid from the container in the liquid-tight state, a liquid ripples when placing or removing the lid and the cell sheet may become damaged in some cases.

The device disclosed here is able to efficiently achieve a liquid-tight state with simple operation and can prevent ripples of a liquid during placing and removing operation of a lid.

The disclosed device includes a container for accommodating a fragile object, a lid member for sealing the container, and a protecting member. The device is configured to form a liquid-tight space by covering a liquid surface in the container, which accommodates the fragile object and a liquid, with the protecting member. The protecting member and an open top of the container are covered with the lid member.

The protecting member and/or the lid member may be subjected to a water-repellent treatment.

The protecting member may exhibit flexibility.

The protecting member may be fluid-impermeable.

The protecting member is configured to be sandwiched between the lid member and the container.

The container may be configured to include a space that houses a pressed-out liquid.

The device may be configured to accommodate a fragile object that is a sheet-shaped cell culture.

The sheet-shaped cell culture may be a laminate.

According to another aspect, a device for holding a fragile object in liquid to prevent damage to the fragile object, comprises a container with a closed bottom and an open top, wherein the container surrounds a space to accommodate the liquid and the fragile object, a lid configured to close the open top of the container and seal the container when the liquid fills the space in the container and the fragile object is in the liquid so that the space is a liquid-tight space; and a protecting member. The protecting member is positionable, when the lid closes the open top of the container while the liquid fills the space and the fragile object is in the liquid, between the lid and a top surface of the liquid so the protecting member contacts the top surface of the liquid and the lid is spaced from the liquid. The lid is separate from the protecting member so that upon removing the lid from the container the lid separates from the protecting member and does not cause ripples in the liquid that might otherwise damage the fragile object in the liquid.

Another aspect of the disclosure here involves a clip that includes a cover member and a base member which are configured to press and sandwich the above-described device from above and below.

In accordance with another aspect of the disclosure here, a method of protecting a fragile object in a liquid comprises: positioning the fragile object and the liquid in a container that includes a closed bottom and an open top, wherein the liquid fills a space in the container from the closed bottom to the open top so that a top surface of the liquid is exposed at the open top of the container; positioning a protecting member in direct contact with the top surface of the liquid that is exposed; and covering the container with a lid so that the space is a liquid-tight space, wherein the lid is separate from the protecting member, and the covering of the container with the lid occurs after the protecting member is positioned in direct contact with the top surface of the liquid that is exposed.

In the device disclosed here, since a liquid-tight state can be efficiently achieved with a simple mechanism and simple operation, the device is greatly advantageous in terms of operability and production costs. Because the inside of the container can be completely brought into the liquid-tight state, bubbles (gas) do not enter the container. Thus, the bubbles do not move in the container and the fragile object is not damaged due to shaking of the container during transportation. In particular, in a case where the fragile object is a laminate of sheet-like cell cultures, the bubbles do not move and thus the laminate does not shift or break. Therefore, the fragile object can be preserved over the long term while maintaining a shape of the fragile object in the liquid and preventing deformation.

In addition, because a liquid-tight state can be easily released, vibration of the container and generation of flow of the liquid, which are caused, for example, by an operator forcibly removing the lid member, can be suppressed, and thus the fragile object is not damaged. In addition, because the operation can be performed without contaminating the surroundings, the device is appropriate to use at a place where cleanliness is strictly controlled, such as a bio-clean room used in producing a sheet-like cell culture and an intensive care unit where a sheet-like cell culture is used.

DETAILED DESCRIPTION

A fragile object as described here refers to an object that has relatively low physical strength and can crack, be damaged, and be deformed due to shaking of a liquid. Examples of a shape of such an object include an object having a thin portion, an object having a band shape (band-shaped object), and an object having a sheet shape (sheet-shaped object). Examples of such an object having a sheet shape include, but are not particularly limited to, sheet-like structures, for example, a flat membrane tissue made of a material derived from a living body, such as a sheet-like cell culture, and films made of various materials, such as plastic, paper, a woven fabric, a nonwoven fabric, a metal, a polymer, and a lipid. Among the examples, it is preferable to use a structure which is hardly decomposable in a liquid and a structure which is hardly disintegratable in a liquid. The sheet-like structure may be polygonal or circular in plan view, and may or may not be uniform in terms of a width, a thickness, and a diameter. One sheet-like structure disclosed here may be used in a single-layer state, or the sheet-like structure may be used in a state of a laminate, in which two or more sheets overlap each other. In a case of the latter, layers of the laminate may be interlocked with each other, or may not be interlocked with each other. In an interlocked case, all overlapping portions may be interlocked with each other or may be partially interlocked with each other. In addition, the term "fragile" as used in the description here means that, for example, it is difficult or practically impossible to perform evaluation of tensile properties with a tensile tester of the related or known art (for example, a tensile tester described in JIS K 7161), in which an object is fixed to a gripper outside a liquid, due to fragility thereof. An example of such a fragile object includes an object which has a small value of each of the tensile properties and is difficult to be accurately measured with the tensile tester of the related or known art. Examples of such a fragile object include objects that exhibit a fracturing load of less than 10 newtons (N), less than 5 N, less than 2 N, less than 1 N, less than 0.5 N, less than 0.1 N, and less than 0.05 N in a tensile test. In addition, since a measurement limit of a tensile test of the related or known art is generally approximately 1 N as a fracturing load, an object exhibiting a fracturing load that falls short of the measurement limit (for example, less than 0.5 N) is preferable as a fragile object according to one aspect representing an example of the disclosure here.

In the description here, the term "graft" refers to a fragile object derived from a living body that has relatively low physical strength. The graft includes a cultured cell (for example, a cell culture) and a harvested cell. The graft further includes a product produced by cells. In addition to the cells and/or the cell products, the graft can also include a material (a supplementary material or a support material) for supplementing and/or supporting a predetermined part of a living body (for example, a target lesion). The graft can take various shapes such as a sheet-like shape, a film-like shape, a block-like shape, and a columnar shape. The graft is used for transplant into a living body. Examples of the graft include a three-dimensional cell tissue (an organoid and a spheroid) and a two-dimensional cell tissue (a sheet-like cell culture). In the disclosure here, the sheet-like (sheet-shaped) cell culture refers to a cell culture in which cells are interlocked with each other to form a sheet-like shape (sheet-shape). The cells may be interlocked with each other directly (including going through a cell element such as an adhesion molecule) and/or via a mediator. The mediator is not particularly limited insofar as the mediator is a substance capable of at least physically (mechanically) interlocking cells with each other, and an example thereof includes an extracellular matrix. The mediator is preferably derived from cells, and is particularly derived from cells configuring the sheet-like cell culture. Although cells are at least physically (mechanically) interlocked with each other, the cells may be functionally, including chemically and electrically, interlocked with each other. The sheet-like cell culture may be configured by one cell layer (a single layer) or configured by two or more cell layers (a multi-layer body). In addition, the sheet-like cell culture may have a three-dimensional structure having a thickness exceeding a thickness of one cell without cells showing a clear layer structure. For example, in a vertical cross-section of the sheet-like cell culture, cells may exist in a non-uniformly (for example, in a mosaic) disposed state instead of being uniformly arranged in a horizontal direction. The sheet-like cell culture may exist as an independently formed single (one-sheet) sheet-like cell culture, or may exist as a laminate that is formed by laminating two or more layers of the independent single (one-sheet) sheet-like cell culture. The laminate may be, for example, a laminate in which two layers (two sheets), three layers (three sheets), four layers (four sheets), five layers (five sheets), or six layers (six sheets) of the sheet-like cell cultures are laminated.

The sheet-like cell culture may be configured by any cells capable of forming the structure. Examples of such cells include, but are not limited to, adherent cells (adhesive cells). Examples of the adherent cells include adherent somatic cells (for example, cardiomyocytes, fibroblasts, epithelial cells, endothelial cells, hepatocytes, pancreatic cells, kidney cells, adrenal cells, periodontal ligament cells, gingival cells, periosteal cells, skin cells, synovial cells, and chondrocytes) and stem cells (for example, myoblasts, tissue stem cells such as cardiac stem cells, pluripotent stem cells such as embryonic stem cells, induced pluripotent stem (iPS) cells, and mesenchymal stem cells). The somatic cells may be cells differentiated from stem cells, particularly iPS cells. Non-limiting examples of cells capable of forming the sheet-like cell culture include myoblasts (for example, skeletal myoblasts), mesenchymal stem cells (for example, cells derived from bone marrow, adipose tissues, peripheral blood, skin, hair roots, muscle tissues, endometrium, placenta, and cord blood), cardiomyocytes, fibroblasts, cardiac stem cells, embryonic stem cells, iPS cells, synovial cells, chondrocytes, epithelial cells (for example, oral mucosal epithelial cells, retinal pigment epithelial cells, and nasal mucosal epithelial cells), endothelial cells (for example, vascular endothelial cells), hepatocytes (for example, hepatic parenchymal cells), pancreatic cells (for example, pancreatic islet cells), kidney cells, adrenal cells, periodontal ligament cells, gingival cells, periosteal cells, and skin cells. In the present specification, cells forming a single-layer cell culture, such as myoblasts and cardiomyocytes, are preferable, and skeletal myoblasts or iPS cell-derived cardiomyocytes are particularly preferable.

The cells can be derived from any organisms that can be treated with a cell culture. Examples of such organisms include, but are not limited to, humans, non-human primates, dogs, cats, pigs, horses, goats, and sheep. In addition, although one type of cells may be used in forming the sheet-like cell culture, two or more types of cells can be used as well. According to a preferable form, in a case where there are two or more types of cells forming a cell culture, for example, in a case of skeletal myoblasts, the proportion (purity) of the largest number of cells is 65% or more, preferably 70% or more, and more preferably 75% or more at the time of a cell culture production end.

The sheet-like cell culture may be a sheet-like cultured tissue obtained by disseminating and culturing cells in a scaffold (a scaffold at the time of cell culturing), but is preferably formed only of substances derived from cells forming the cell culture and does not include substances other than the substances derived from cells.

The sheet-like cell culture may be produced through any known techniques.

In one form, the sheet-like cell culture may be a sheet-like skeletal myoblast culture. Since the sheet-like skeletal myoblast culture is fragile to a point that the sheet-like skeletal myoblast culture fractures due to its own weight when a part thereof is grasped, the sheet-like skeletal myoblast culture cannot be transported alone in the related art and it is extremely difficult to return to an original shape thereof once folded. Therefore, it is significant to maintain a sheet shape in a liquid.

According to the disclosure here, a container is not particularly limited insofar as the container can accommodate a fragile object and a liquid, and the liquid does not leak, and any container including a commercially available container can be used. Examples of a material from which the container may be fabricated include, but are not limited to, polyethylene, polypropylene, Teflon (registered trademark), polyethylene terephthalate, polymethyl methacrylate, nylon 6,6, polyvinyl alcohol, cellulose, silicon, polystyrene, glass, polyacrylamide, polydimethylacrylamide, and metals (for example, iron, stainless steel, aluminum, copper, and brass). In addition, it is preferable that the container has at least one flat bottom surface for maintaining the shape of the fragile object, and examples thereof include, but are not limited to, a petri dish, a cell culture dish, and a cell culture bottle. Although not particularly limited, the area of the flat bottom surface is typically 1.13 to 78.5 $cm^2$, preferably 12.6 to 78.5 $cm^2$, and more preferably 9.1 to 60.8 $cm^2$.

According to one aspect of the disclosure here, a liquid in the container is configured to include at least one type of component, and the component is not particularly limited. For example, the liquid may be configured by a liquid such as water, an aqueous solution, a non-aqueous solution, a suspension, and an emulsion.

In the present specification, a solution or a liquid may be a liquid having fluidity as a whole, or may include solid substances such as cell scaffolds and other non-liquid components such as bubbles.

The component configuring the liquid in the container is not particularly limited insofar as an effect on the fragile object is small. In a case where the fragile object is a membrane made of a material derived from a living body, it is preferable that the component configuring the liquid in the container is, from a perspective of biological stability and long-term preservability, a biocompatible component, that is, a component which does not cause undesired effects such as inflammatory reaction, immune reaction, and poisoning reaction or at least has a small effect on a biological tissue or a cell. Examples of the component include water, a physiological salt solution, physiological buffers (for example, HBSS, PBS, EBSS, Hepes, and bicarbonate sodium), culture media (for example, DMEM, MEM, F12, DMEM/F12, DME, RPMI1640, MCDB, L15, SkBM, RITC80-7, and IMDM), sugar solutions (a sucrose solution and Ficoll-paque (registered trademark) PLUS), seawater, a serum-containing solution, a Renografin (registered trademark) solution, a metrizamide solution, a meglumine solution, glycerin, ethylene glycol, ammonia, benzene, toluene, acetone, ethyl alcohol, benzol, an oil, a mineral oil, animal fat, a vegetable oil, an olive oil, a colloid solution, liquid paraffin, a turpentine oil, a linseed oil, and a castor oil.

In a case where the fragile object is a sheet-like cell culture, it is preferable that the component configuring the liquid in the container is a component which can stabilize and preserve cells, contains minimum oxygen and nutrients necessary for cell survival, and does not destroy cells due to osmotic pressure. Examples of the component include, but are not limited to, a physiological salt solution, physiological buffers (for example, HBSS, PBS, EBSS, Hepes, and bicarbonate sodium), culture media (for example, DMEM, MEM, F12, DMEM/F12, DME, RPMI1640, MCDB, L15, SkBM, RITC80-7, and IMDM), and sugar solutions (a sucrose solution and Ficoll-paque PLUS (registered trademark)).

The amount of the liquid in the container is preferably such that the fragile object can be maintained in a state where a lid member is attached to the container, and the amount is not particularly limited insofar as a liquid volume formed between a bottom portion of the container and a top of the lid member is approximately at a height that the fragile object does not fluctuate (shake) in the liquid. That is, when a space is generated between a liquid surface and the lid member, the liquid (liquid surface) can shake, and so the fragile object is also likely to shake. Thus, it is preferable that the liquid volume is adjusted such that the space is not generated between the liquid surface and the lid member (i.e., there is no space between the liquid surface and the inside surface of the lid member). According to one possible form, the sheet-like cell culture has a diameter of approximately 35 to 55 mm and an area of 6 cm$^2$ or more. The liquid volume is, for example, 1.0 mm to 20.0 mm regardless of the diameter of the sheet-like cell culture.

The lid member (lid) is not particularly limited insofar as the container can be sealed. Examples of a material from which the lid member may be fabricated include, but are not limited to, polyethylene, polypropylene, Teflon (registered trademark), polyethylene terephthalate, polymethyl methacrylate, nylon 6,6, polyvinyl alcohol, cellulose, silicon, polystyrene, glass, polyacrylamide, polydimethylacrylamide, and metals (for example, iron, stainless steel, aluminum, copper, and brass).

The shapes of the lid member and the container are not particularly limited insofar as the lid member and the container can be engaged with each other and a sealed space can be formed due to such engagement.

For example, in a case where the container is a general-purpose petri dish, it is preferable that the shape of the lid member is circular. In addition, a state of the fragile object accommodated in the container and the presence or absence of bubbles in the liquid may be checked by making the lid member and/or the container of a light-transmitting material.

The fragile object is held in the liquid in the container where the liquid is accommodated. Although a position of the fragile object in the liquid is not particularly limited, the fragile object is disposed at a position in which the lid member and the fragile object do not come into contact with each other (or may come into contact with each other) in a state where the lid member is attached to the container to form the sealed space. Preferably, in the liquid of the container, the fragile object is disposed above a bottom of the container or near the bottom.

In the description here, a "water-repellent treatment" refers to treating a solid surface such that a contact angle, which is an angle formed between a liquid surface and a solid surface, is 90° or more at a boundary line where the solid surface and the liquid are in contact with each other. For example, on a water-repellent solid surface which is subjected to a Teflon (registered trademark) treatment, the contact angle is close to 180° and liquid droplets become almost spherical. Therefore, even when the liquid is interposed between individual surfaces which are subjected to the water-repellent treatment, the individual surfaces do not stick to each other. An example of a water-repellent treatment method includes a coating method of adhering a resin, such as Teflon (registered trademark), silicon, a fluorine-based water repellent, a waxy resin, an alumina soap, pyridinium salt, and ceratin, to the solid surface. In addition, a method of executing an unevenness treatment on the solid surface without using a coating agent, such as forming unevenness on the solid surface through a laser treatment just as a super-water-repellent treatment, may be adopted. The solid surface is thus treated in a way that causes the solid surface to be uneven so that the solid surface is less likely to attract water/liquid.

One aspect of the disclosure here relates to a device including a container for accommodating a fragile object, a lid member (lid) for sealing the container, and a protecting member, the device being capable of forming a liquid-tight space by covering a liquid surface in the container which accommodates the fragile object and a liquid with the protecting member and further covering the protecting member and an opening portion of the container with the lid member.

Set forth below with reference to the accompanying drawings is a detailed description of embodiments of a fragile object holding device with a protecting mechanism representing examples of the inventive fragile object holding device with protecting mechanism disclosed here.

Initially, a first embodiment of the fragile object holding device with protecting mechanism will be described.

Figure 1A:
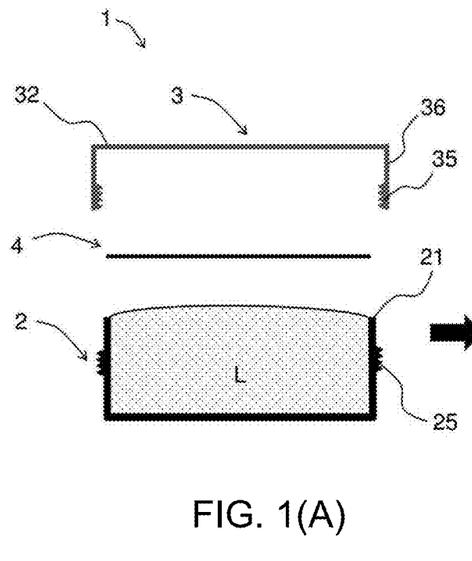
FIGS. 1(A) and 1(B) are cross-sectional views of a device 1 according to a first embodiment.
Figure 1B:
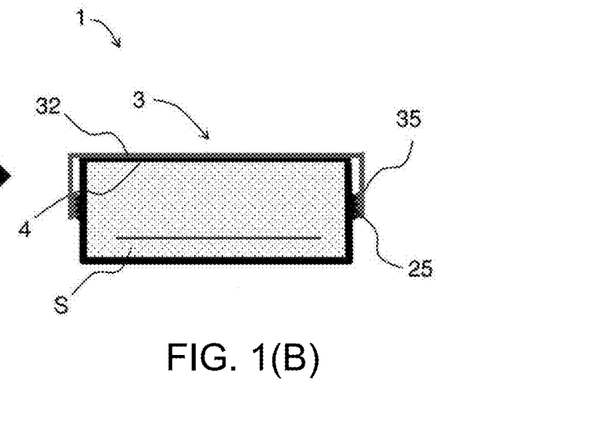
Figure 2A:
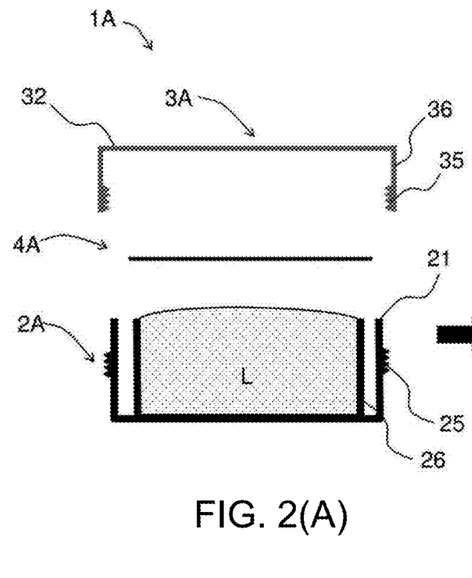
FIGS. 2(A) and 2(B) are cross-sectional views of a device 1A according to a second embodiment.
Figure 2B:
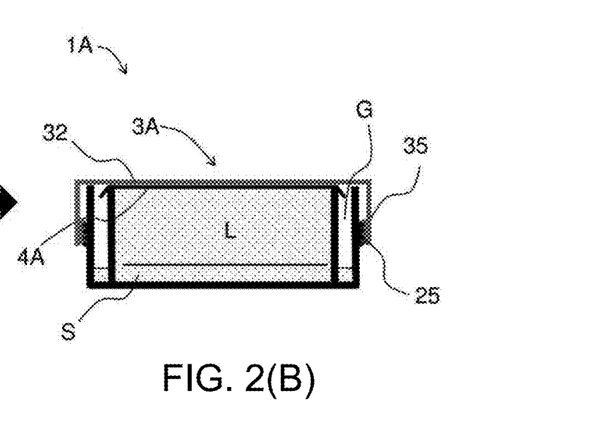
Figure 3A:
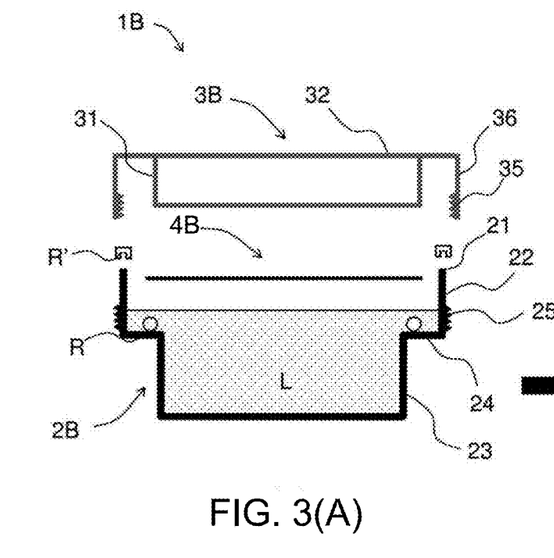
FIGS. 3(A) and 3(B) are cross-sectional views of a device 1B according to a third embodiment.
Figure 3B:
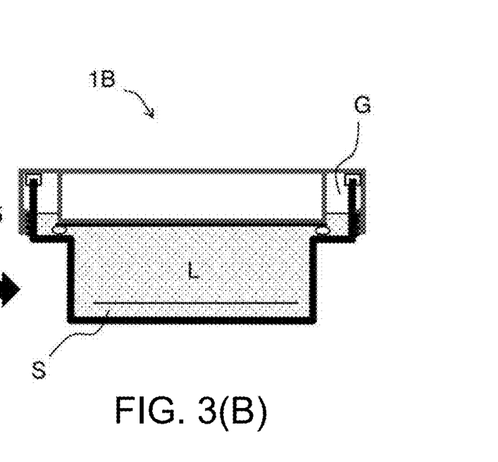

FIGS. 1(A) and 1(B) are cross-sectional views of a device 1 according to a first embodiment. FIGS. 2(A) and 2(B) are cross-sectional views of a device 1A according to a first modification example of the first embodiment. FIGS. 3(A) and 3(B) are cross-sectional views of a device 1B according to a second modification example of the first embodiment. In each of the accompanying drawings, for ease of description, the size of each of members or features is enlarged as appropriate, and so the illustrated members or features are not shown in actual size.

As illustrated in FIG. 1(A), the device 1 according to a first embodiment includes a container 2, a lid member or lid 3 for sealing the container 2, and a protecting member or protector 4. The container 2 has a shape of a general-purpose petri dish having a rim portion (annular rim) 21 that circumferentially surrounds an opening portion (open top of the container) and configures or defines an accommodation space that can accommodate a fragile object S. In the illustrated embodiment, the rim portion 21 extends from a bottom of the container. The lid member 3 includes a top plate portion (plate-shaped top) 32, a tubular circumferentially extending skirt wall 36 hanging down from a rim of the top plate portion 32, and a female screw portion (threaded portion) 35 provided on an inner peripheral surface of the tubular skirt wall 36. The female screw portion 35 is screwed to or mates with (threadedly engages) a male screw portion (threaded portion) 25 provided on an outer peripheral surface of the container 2 to cause the lid member 3 to be screwed with the container 2. The outer diameter of the protecting member 4 is larger than the diameter (outer diameter) of the rim portion 21 of the container 2. That means also that the outer diameter of the protecting member 4 is larger than the inner diameter of the rim portion 21 of the container 2 as shown in FIG. 1(B). The protecting member 4 is a fluid-impermeable plate-like member that can cover the opening portion of the container 2. The protecting member 4 and the lid member 3 are subjected to water-repellent treatment.

As illustrated in FIGS. 1(A) and 1(B), when using the device 1, the container 2 accommodates a liquid L and the fragile object S. At this time, by further adding the liquid L in a state where the container 2 is full with the liquid L, a convex surface is formed on a liquid surface (exposed surface) due to surface tension of the liquid L (FIG. 1(A)). Next, the protecting member 4 in an inclined state is placed on the liquid surface, and comes into close contact with the rim portion 21 while pressing and leveling the convex surface. Since the container 2 is sealed with the protecting member 4 as described above, in a case where there are bubbles in the liquid surface, the inclined protecting member 4 applies a buoyant force to bubbles, and thereby the bubbles can be reliably pressed out. Then, by covering the protecting member 4 and the container 2 with the lid member 3, the protecting member 4 is sandwiched between the container and the lid member, and thereby a liquid-tight state in the container 2 is formed. In addition, even in a case where a gas has entered between the lid member 3 and the protecting member 4 at this time, the fluid-impermeable protecting member 4 blocks the gas. Thus, bubbles do not enter the container 2 and the fragile object S is not damaged.

When using the fragile object S, the lid member 3 is removed from the container 2. At this time, since the protecting member 4 and the lid member 3 are subjected to the water-repellent treatment, the protecting member 4 does not stick to the lid member 3. Therefore, even when the lid member 3 is removed from the container 2, the protecting member 4 can keep a liquid-tight state in the container 2. Next, as the protecting member 4 is removed by sliding the protecting member 4 in a horizontal direction and releasing the liquid-tight state, the protecting member 4 can be easily removed from the container 2. That is, in a case where there is no protecting member 4 between the lid member 3 and the container 2, the lid member 3 and the liquid surface come into direct and close contact with each other, and the lid member 3 pulls the liquid due to surface tension when removing the lid member 3. At the same time, when removing the lid member 3 from the container 2 in the liquid-tight state, a sudden force is applied to the lid member 3. Thus, the liquid surface ripples and the fragile object becomes damaged in some cases. In contrast, the device disclosed here is able to avoid or prevent such problem by protecting the liquid surface with the protecting member 4. The protecting member 4 thus functions as a protecting mechanism that protects the liquid surface. Dimensional errors of the device 1 in a vertical direction and the horizontal direction may be absorbed by having an elastic seal member (for example, a packing) interposed between the container 2, the lid member 3, and the protecting member 4.

In the device 1 according to the first embodiment disclosed here as one example of the inventive device disclosed here, since a liquid-tight state can be efficiently achieved with a simple mechanism and simple operation, the device is quite advantageous in terms of operability and production costs. Since the inside of the container can be completely brought into the liquid-tight state, bubbles (gas) do not enter the container. Thus, the bubbles do not move in the container and the fragile object is not damaged due to shaking of the container during transportation. In particular, in a case where the fragile object is a laminate of sheet-like or sheet-shaped cell cultures, the bubbles do not move and thus the laminate does not shift or break. Therefore, the fragile object can be preserved over the long term while maintaining a shape of the fragile object in the liquid and preventing deformation.

In addition, in the device 1 according to the first embodiment, since a liquid-tight state can be easily released, vibration of the container and generation of flow of the liquid, which are caused, for example, by an operator forcibly removing the lid member, can be suppressed, and thus the fragile object is not damaged.

Next, a second embodiment representing another example of the inventive device disclosed here will be described. In the description below, features that are the same or similar to those described above are identified by the same reference numerals and a detailed description of such features is not repeated. In each of the drawings in the present application, for ease of description, the size of each of members is enlarged as appropriate, and each of the illustrated members is not shown in the actual size.

As illustrated in FIG. 2(A), the device 1A according to the second embodiment includes a container 2A, a lid member 3A for sealing the container 2A, and a protecting member 4A. The container 2A has a shape of a general-purpose petri dish having the rim portion 21 that circumferentially surrounds the opening portion, and has a tubular wall 26 that protrudes upward from a bottom portion. The tubular wall 26 is an annular wall that is positioned radially inwardly of the rim portion 21 so that an annular space exists between the outwardly facing surface of the tubular wall 26 and the inwardly facing surface of the rim portion 21. An accommodation space that can accommodate the fragile object S is formed inside the tubular wall 26 of the container 2A. A height of the tubular wall 26 is the same as a height of the rim portion 21 of the container 2A. When the lid member 3A is attached to the container 2A, the lid member can come into close contact with both of the rim portion 21 of the container 2A and a rim portion of the tubular wall 26. The outer diameter of the protecting member 4A is smaller than the inner diameter of the rim portion 21 of the container 2A, and is larger than the outer diameter of a rim portion or free end portion of the tubular wall 26. In the embodiment, the protecting member 4A has a film shape or is film-shaped, having flexibility, and an inner surface of the lid member 3A is subjected to the water-repellent treatment.

As illustrated in FIGS. 2A and 2B, when using the device 1A, the liquid L and the fragile object S are accommodated inside the tubular wall 26 of the container 2A. At this time, by further adding the liquid L in a state where the accommodation space is full with the liquid L, a convex surface is formed on a liquid surface due to surface tension of the liquid L (FIG. 2(A)). Next, the protecting member 4A is placed on the liquid surface, and comes into close contact with the rim portion 21 while pressing and leveling the convex surface. Since the protecting member 4A has a film shape and can be slowly placed on the liquid surface, the liquid does not ripple. In addition, since a convex portion of the liquid L pressed out by the protecting member 4A is received by a space G outside the tubular wall 26 of the container 2A, the surroundings are not contaminated and the liquid L does not enter between the protecting member 4A and the lid member 3A. Therefore, when removing the lid member 3A, the protecting member 4A does not stick to the inside of the lid member 3A. Since the protecting member 4A can be sandwiched between the lid member 3A and the container 2A with a strong force by screwing the lid member 3A with the container 2A, liquid-tightness in the accommodation space can be maintained, and simultaneously the liquid L in the space G does not leak to the outside.

When using the fragile object S, the lid member 3A is removed from the container 2A. Since unevenness is formed in a plurality of places on the inner surface of the lid member 3A, the protecting member 4A does not stick to the inside of the lid member 3A. Therefore, even when the lid member 3A is removed from the container 2A, the protecting member 4A can keep a liquid-tight state in the container 2A. Next, as the protecting member 4A is peeled off or pulled off from the liquid surface, a contact area with the liquid surface gradually decreases. Thus, ripples in the liquid surface can be suppressed to a minimum. That is, in a case where the inner surface of the lid member 3A and the liquid surface are in contact with each other (i.e., there is no protecting member 4A), the lid member 3A pulls the liquid surface when the lid member 3A is being removed, and a repulsive force is generated at a moment when the lid member 3A comes off, thereby generating vibration in the liquid surface. On the other hand, in a case where the protecting member 4A is interposed between the container and the lid member, the vibration is not transmitted to the fragile object S since the protecting member 4A protects the liquid surface. Dimensional errors of the device 1A in the vertical direction and the horizontal direction may be absorbed by having an elastic seal member (for example, a packing) interposed between the container 2A, the lid member 3A, and the protecting member 4A.

In the device 1A according to the second embodiment of the present application, since a liquid-tight state can be efficiently achieved with a simple mechanism and simple operation, the device is greatly advantageous in terms of operability and production costs. Since the inside of the container can be completely brought into the liquid-tight state, bubbles (gas) do not enter the container. Thus, the bubbles do not move in the container and the fragile object is not damaged due to shaking of the container during transportation. In particular, in a case where the fragile object is a laminate of sheet-like or sheet-shaped cell cultures, the bubbles do not move and thus the laminate does not shift or break. Therefore, the fragile object can be preserved over the long term while maintaining a shape of the fragile object in the liquid and preventing deformation.

In addition, in the device 1A according to the second embodiment of the present application, since a liquid-tight state can be easily released, vibration of the container and generation of flow of the liquid, which are caused, for example, by an operator forcibly removing the lid member, can be suppressed, and thus the fragile object is not damaged.

Next, a third embodiment representing another example of the inventive device disclosed here will be described. In the description below, features that are the same or similar to those in the embodiments described above are identified by the same reference numerals and a detailed description of such features is not repeated. Note that in each of the drawings in the present application, for ease of description, the size of each of members is enlarged as appropriate, and each of the illustrated members is not shown in the actual size.

As illustrated in FIG. 3(A), the device 1B according to the third embodiment includes a container 2B, a lid member 3B for sealing the container 2B, and a protecting member 4B. The container 2B is a bottomed tubular container including an upper portion 22 and a lower portion 23, and the lower portion 23 configures or defines a space that can accommodate the fragile object S. An inner diameter of the upper portion 22 is larger than an inner diameter of the lower portion 23, and a stepped portion 24 is provided at a boundary between the upper portion 22 and the lower portion 23. The lid member 3B has a projection portion 31 that protrudes downward from the top plate portion (plate-shaped top) 32. In the illustrated embodiment shown in FIGS. 3(A) and 3(B), the lid member 31 includes an annular part that extends axially from the plate-shaped top 32 and a plate-shaped part that contacts the protecting member 4B during use. In the embodiment, the protecting member 4B is sandwiched between the projection portion 31 and the stepped portion 24, and a packing R for improving adhesion is provided between the protecting member 4B and the stepped portion 24. The protecting member 4B has a plurality of small holes that pass through the protecting member 4B, and can cause the liquid L to permeate through the protecting member 4B. In addition, a packing R' having a U-shaped cross-sectional shape is provided between the rim portion 21 of the container 2B and the lid member 3B, and thus dimensional errors of the device 1B in the vertical direction and the horizontal direction can be absorbed.

As illustrated in FIGS. 3A and 3B, when using the device 1B, the container 2B accommodates the liquid L and the fragile object S. At this time, the liquid L fills up to a height exceeding the stepped portion 24, and the protecting member 4B is placed on the stepped portion 24 while inclining the protecting member. Next, the protecting member 4B is sandwiched between the projection portion 31 and the stepped portion 24 of the container 2B by screwing the lid member 3B to the container 2B. Then, as the projection portion 31 (the plate-shaped part of the projection portion 31) presses the protecting unit 4B, the packing R interposed between the protecting unit 4B and the stepped portion 24 is pressed flat, thereby improving a liquid-tight state formed in the lower portion 23 of the container 2B. The liquid L pressed out by the projection portion 31 is housed in the space G between the upper portion 22 of the container 2B and the projection portion 31. When using the fragile object S, the lid member 3B is removed from the container 2B. Since surface tension is not generated between the protecting member 4B and the lid member 3B by virtue of the plurality of small holes provided in the protecting member 4B, the protecting member 4B does not stick to the inside of the lid member 3B. In addition, when the lid member 3B is removed, spaces of the lower portion 23 and the upper portion 22 of the container 2B communicate with each other via the plurality of small holes in the protecting member 4B, that is, a liquid-tight state is released. Thus, the protecting member 4B is easily removed, and thus the fragile object can be taken out.

In the device 1B according to the third embodiment of the present application, since a liquid-tight state can be efficiently achieved with a simple mechanism and simple operation, the device is greatly advantageous in terms of operability and production costs. Since the inside of the container can be completely brought into the liquid-tight state, bubbles (gas) do not enter the container. Thus, the bubbles do not move in the container and the fragile object is not damaged due to shaking of the container during transportation. In particular, in a case where the fragile object is a laminate of sheet-like or sheet-shaped cell cultures, the bubbles do not move and thus the laminate does not shift or break. Therefore, the fragile object can be preserved over the long term while maintaining a shape of the fragile object in the liquid and preventing deformation.

In addition, in the device 1B according to the third embodiment, since a liquid-tight state can be easily released, vibration of the container and generation of flow of the liquid, which are caused, for example, by an operator forcibly removing the lid member, can be suppressed, and thus the fragile object is not damaged.

Although the illustrated embodiments representing examples of the inventive device disclosed here have been described hereinbefore, the present invention is not limited thereto. The lid members 3, 3A, and 3B, the containers 2, 2A, and 2B, and the protecting members 4, 4A, and 4B according to the first to third embodiments can be freely combined with each other.

In the present invention, each configuration or feature can be replaced with other configurations or features that can fulfill or perform the same or similar function, or other configurations or features can be added.

The use of the fragile object, in which the device disclosed here is usable, can be performed, for example, through the following steps in turn.

(1) Accommodate the liquid and the fragile object in the container.

(2) Protect the liquid surface in the container with the protecting member.

(3) Cover the container with the lid member to form a liquid-tight state.

(4) Transport the device.

(5) Remove the lid member to release the liquid-tight state.

(6) Remove the protecting member.

(7) Take out and use the fragile object.

Hereinafter, an embodiment of a clip suitable for pressing and sandwiching the device (the container and the lid member) disclosed here will be described in detail with reference to the drawings.

Figure 4:
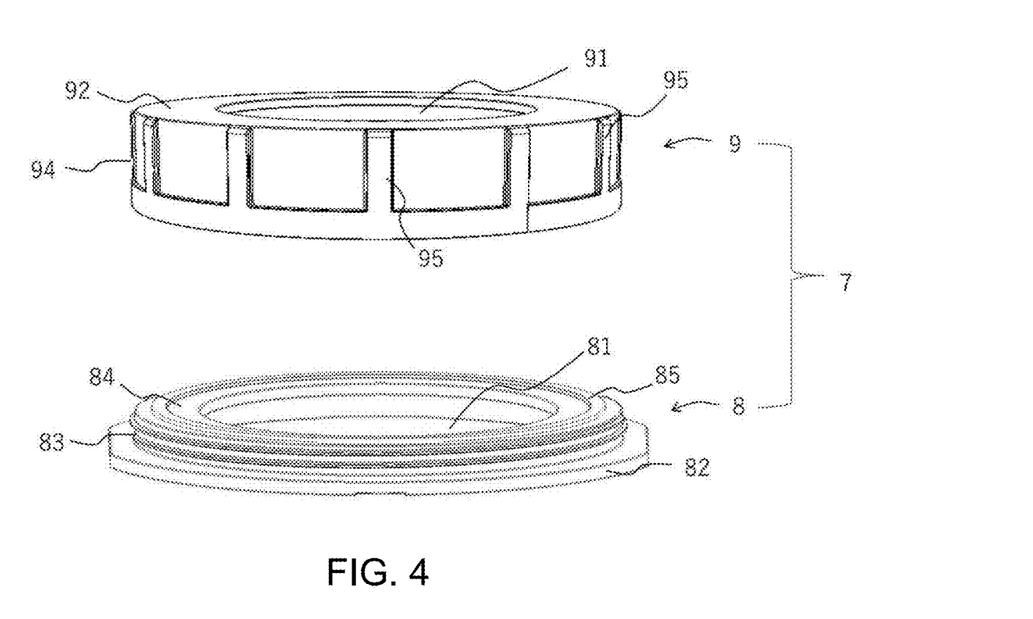
FIG. 4 is a perspective view of a clip 7 according to a fourth embodiment.
Figure 5:
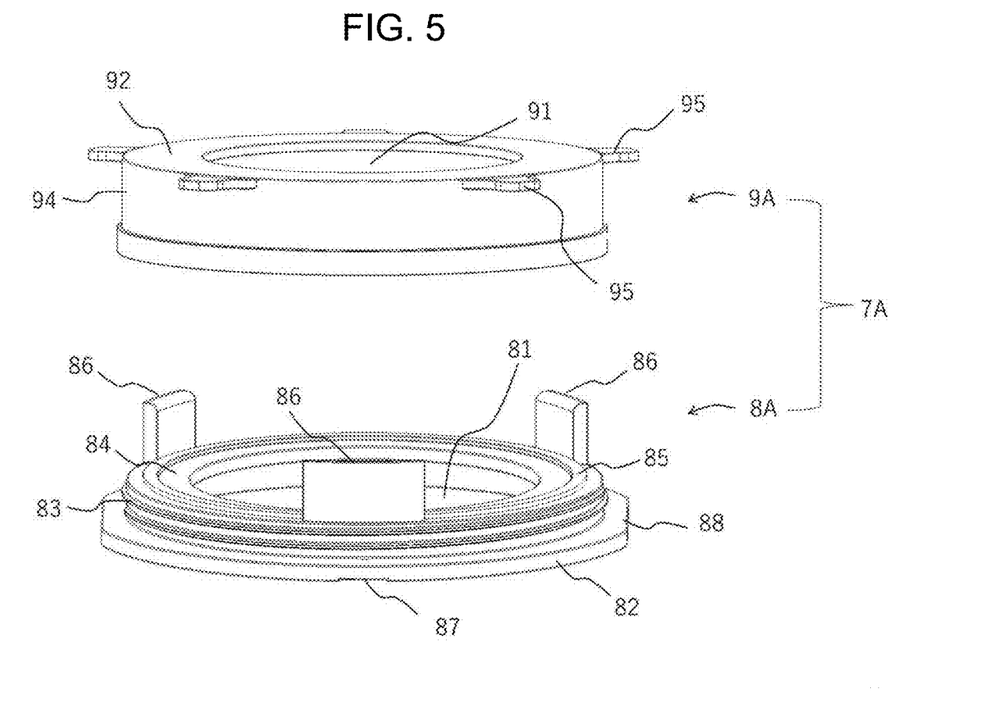
FIG. 5 is a perspective view of a clip 7A according to a fifth embodiment.
Figure 6:
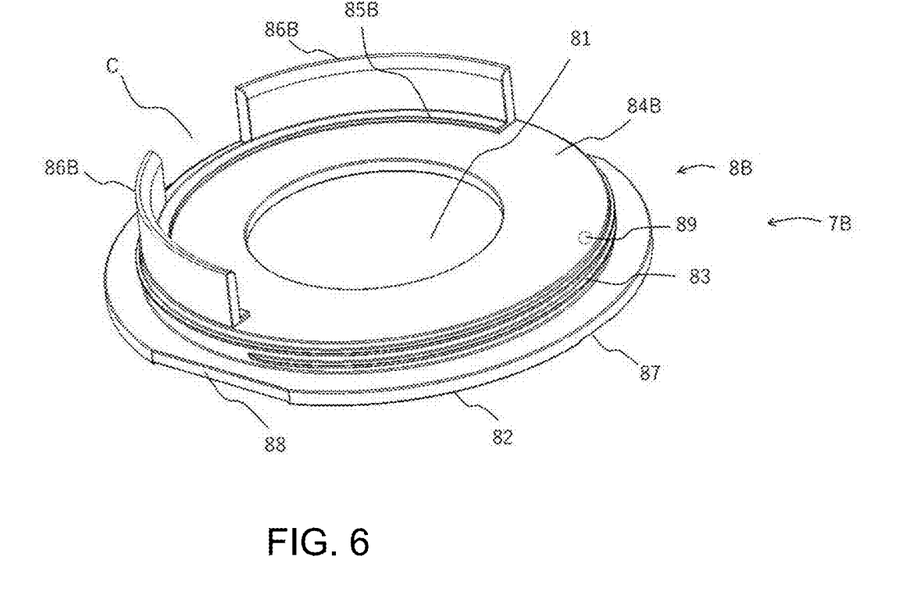
FIG. 6 is a perspective view of a clip 7B according to a sixth embodiment.

FIG. 4 is a perspective view of a clip 7 according to an embodiment. FIG. 5 is a perspective view of a clip 7A according to another embodiment. FIG. 6 is a perspective view of a clip 7B according to a further embodiment of the present invention. In each of the drawings in the present application, for ease of description, the size of each of members is enlarged as appropriate, and each of the illustrated members is not shown in the actual size.

The clip 7 can press and sandwich the device including the container and the lid member for sealing the container from above and below.

Both the base member 8 and the cover member 9 have a circular shape, and can appropriately press the device from above and below. The base member 8 includes an opening portion 81, a bottom portion 82, a screwing portion (engagement portion) 83, a placement portion 84, and a ridge portion 85. In this embodiment, the engagement occurs by screwing or threaded engagement. The placement portion 84 has a placement surface as an upper surface on which the container can be placed, and the opening portion 81 is provided in a center portion of the placement portion 84. The placement portion 84 has the annular ridge portion 85 (elongated ridge) that surrounds a lower end of the container and can define a position where the container is positioned with respect to the base member 8, when the container is placed on the placement surface. The placement portion 84 has a disk shape that protrudes upward from the bottom portion 82, and the screwing portion 83 is provided on the outer peripheral side surface of the placement portion 84. The bottom portion 82 has an outer diameter larger than an outer diameter of the placement portion 84, and serves a role of a bottom portion when providing the base member 8 on a table.

The cover member 9 includes an opening portion 91 (opening), a top portion 92 (top), a screwing portion (engagement portion), a tubular skirt wall 94, and a grip portion 95. The top portion 92 has a cover surface that can cover an upper surface of the lid member, and the opening portion 91 is provided in a center portion of the top portion 92. The top portion 92 includes the tubular skirt wall 94 extending or projecting down from a rim of the top portion 92, and the device can be sandwiched by being surrounded with the top portion 92, the tubular skirt wall 94, and the placement portion 84. The screwing portion is provided on an inner peripheral surface of a lower end portion of the tubular skirt wall 94, and the cover member 9 can be screwed to the base member 8 by screwing or threadedly engaging such a screwing portion with the screwing portion 83 of the base member 8. Optionally, a position where the lid member is provided with respect to the clip 7 can also be defined by matching an inner diameter of at least a part of the tubular skirt wall 94 (for example, an inner peripheral surface of an upper end portion of the tubular skirt wall 94) with an outer diameter of the lid member.

When using the clip 7, the container in which is accommodated the object S is covered with the lid member. At this time, optionally, by covering the container with the lid member in a state where the container is full with the liquid L, a liquid-tight space can also be formed. In addition, optionally, by having the seal member interposed at a suitable position between the container and the lid member, sealability can also be improved. Next, the container is positioned on the base member 8. At this time, the container can be positioned at the center of the placement portion 84 using the ridge portion 85. In addition, since the screwing portion 83 of the base member 8 is provided below the placement portion 84, that is, the screwing portion 83 is not a structure that surrounds a side surface of the container, vibration can be suppressed by sliding the container in a lateral direction, when placing/removing the container to/from the placement portion 84. Next, the cover member 9 is attached to the base member 8. At this time, the lid member can also be positioned at the center of the cover member 9 (and the base member 8) using the tubular skirt wall 94.

As described above, the clip 7 can define relative positions of the container and the lid member using the ridge portion 85 of the base member 8 and the tubular skirt wall 94 of the cover member 9. When the device is sandwiched between the base member and the cover member, the screwing portion 83 of the base member 8 and the screwing portion of the cover member 9 are screwed with each other. At this time, by performing screwing operation by gripping the grip portion 95 provided on the outer peripheral surface of the tubular skirt wall 94 as a protruding portion (may be a groove portion), the container and the lid member can be fastened to each other from above and below with a strong force. This is appropriate for, for example, the use in a case where the container is a container that does not have a screwing portion such as a general-purpose petri dish, and has high versatility. In the devices 1, 1A, and 1B of the first, second and third embodiment, a configuration where the female screw portion 35 and the male screw portion 25 are omitted and the lid member does not rotate (is not screwed) with respect to the container may be adopted. In this case, since torque of the lid member does not reach the protecting member interposed between the container and the lid member, the configuration is particularly advantageous. Then, in particular, in a case where the elastic seal member is interposed, the configuration is advantageous since the seal member is accurately compressed between the container and the lid member of which relative positions are accurately determined, and thus sealablilty improves. It is thus possible to prevent the device from becoming destroyed since it is sufficient that the cover member 9 is screwed by a height of the screwing portion 83 of the base member 8. Also the sandwiching operation is easy, and a sandwiching pressure can be easily adjusted.

Since both of the base member 8 and the cover member 9 have the opening portion 81 and the opening portion 91, respectively, at the center portions, a position where the device is fixed and a state of the liquid L and the accommodation object S accommodated in the device can be observed at all times. This is particularly advantageous in a case where the container and the lid member are made of a light-transmitting material. This is advantageous even when the fragile object is an object having low visibility such as a sheet-like or sheet-shaped cell culture since light can be emitted from one opening portion and the sheet-like cell culture can be viewed from the other opening portion. In addition, in a case of forming a liquid-tight space as described above, the lid member can be pressed against the container while checking if bubbles or foreign substances are mixed in the container via the opening portion 91.

Next, the device is transported. Since the device is firmly sandwiched in the clip 7, a problem that the lid member comes off the container due to shaking during transportation can be prevented. Since the surroundings are surrounded by the clip 7, the device is protected from outside shock. Finally, the clip 7 is removed from the device at a destination and is used.

Although the illustrated embodiments of the device described as examples of the inventive device disclosed here have been described, the present invention is not limited thereto. For example, the screwing portion 83 of the base member 8 and the screwing portion of the cover member 9 can be replaced with other engagement means that has a function of pressing the device from above and below, such as slide engagement (for example, refer to Japanese Patent Application Publication No. 2006-315757), flange fitting (for example, refer to Japanese Patent Application Publication No. 2006-001582), and ridge engagement (for example, refer to Japanese Patent Application Publication No. 2016-203985). The annular ridge portion 85 can be replaced with other structures that can position the container on the placement surface, such as a plurality of annularly disposed protrusions. As the accommodation object S, for example, the fragile object (for example, a laminate of sheet-like or sheet-shaped cell cultures) can also be accommodated. In this case, by making the inside of the container liquid-tight, the fragile object can be transported while maintaining the shape of the fragile object.

Next, an embodiment representing another example of the inventive clip disclosed here will be described. In the description below, features of the clip that are the same or similar to those described above are identified by the same reference numerals and a detailed description of such features is not repeated. Note that in each of the drawings in the present application, for ease of description, the size of each of members is enlarged as appropriate, and each of the illustrated members is not shown in the actual size.

As illustrated in FIG. 5, the clip 7A according to this embodiment includes a base member 8A and a cover member 9A. In the embodiment, the base member 8A further includes protruding walls 86 that are circumferentially spaced apart, a groove portion 87, and a notch portion 88. The plurality of protruding walls 86 are walls that are provided radially outside the ridge portion 85 and protrude from the placement portion 84 to a height exceeding the height of the container. The groove portion 87 is provided in a lower surface of the bottom portion 82 of the base member 8A. Thus, the base member 8A can be prevented from sticking to an operation surface when providing the base member 8A on a table.

When using the clip 7A, the container is positioned at the center of the base member 8A using the ridge portion 85. Next, the lid member can be positioned at the center of the base member 8A by causing the lid member to follow the protruding walls 86 when covering the container with the lid member. That is, an operator can define relative positions of the container and the lid member using the ridge portion 85 and the protruding walls 86 of the base member 8A. This is particularly advantageous in that the seal member can be accurately pressed in a case where the annular seal member is interposed between the container and the lid member.

Next, the device is sandwiched between the base member 8A and the cover member 9A. At this time, screwing operation can be easily performed by gripping the grip portion 95 configured as the protruding portion that radially protrudes from the cover member 9A and the notch portion 88 provided in a side surface of the bottom portion 82 of the base member 8A. When using the device, screwing of the cover member 9A is released to remove the device from the base member 8A. At this time, it is easy to grasp the device since the device is exposed from a gap between the plurality of protruding walls 86. In addition, since the plurality of protruding walls 86 are disposed to surround the container, the lid member can be accurately positioned with respect to the container.

Next, a further embodiment representing another example of the inventive clip disclosed here will be described. In the description below, features that are the same or similar to features in the embodiments of the clip described above are identified by the same reference numerals and a detailed description of such features is not repeated. Note that in each of the drawings in the present application, for ease of description, the size of each of members is enlarged as appropriate, and each of the illustrated members is not shown in the actual size.

As illustrated in FIG. 6, the clip 7B according to this embodiment includes a cover member (not illustrated) and a base member 8B. The base member 8B includes a placement portion 84B, a ridge portion 85B, and protruding walls 86B (description of other configurations will be omitted). The ridge portion 85B is semiannularly disposed on the placement portion 84B. The protruding walls 86B are semiannularly disposed outside the ridge portion 85B, and a notch (gap) C is provided in a part thereof (the two or more protruding walls 86B may be semiannularly disposed with a gap provided). That is, in the embodiment, one half of a placement surface of the placement portion 84B (an opposite side half to the ridge portion 85B and the protruding walls 86B) is configured as a flat surface that is devoid of the ridge portion 85B and the protruding walls 86B.

When using the clip 7B, the container is positioned to slide from an opposite side to the ridge portion 85B and the protruding walls 86B in the lateral direction (a direction of the ridge portion 85B and the protruding walls 86B). That is, the container is positioned near the half of the placement surface of the placement portion 84B that is devoid of the ridge portion 85B and the protruding walls 86B, and the container is slid laterally toward the ridge portion 85B and the protruding walls 86B (i.e., toward the notch C). At this time, by causing the container, which accommodates the object S and the liquid L, to slide on a flat surface of the placement portion 84B, unintended vibration of the container can be suppressed. Next, the lid member is attached to the container. At this time, by pressing the lid member against the protruding walls 86B of the base member 8B, the lid member can be accurately positioned with respect to the container. When using the device (not illustrated), the device is removed from the base member 8B. At this time, by pushing a side surface of the device (the container and/or the lid member) exposed at the notch C, the device is caused to slide on the flat surface and can be removed. A projection portion 89, which is a mark, may be provided on a side facing the notch C on the placement portion 84B such that a sliding direction is easily noticed when sliding the device 1 on the base member 8B. Accordingly, the device 1 can be accurately positioned on the placement portion 84B simply by sliding the device 1 between the projection portion 89 and the notch C. In addition, the device 1 can also be made to not be shifted by adopting a configuration where the projection portion 89 is disposed on an extension line of the ridge portion 85B to face the notch C and the side surface of the device 1 is locked by the projection portion 89.

In the clip according to the embodiments disclosed here, since the container and a lid member can be efficiently brought into close contact with each other with a simple mechanism and simple operation, the device is greatly advantageous in terms of operability and production costs. In addition, since the object accommodated in the container can be viewed from the outside, a state of the accommodated object and mixing of foreign substances can be easily checked. Further, since a relative positional relationship between the container and the lid member can be accurately adjusted, sealablilty improves. In particular, since the seal member can be accurately pressed in a case where the elastic seal member is interposed between the container and the lid member, sealablilty improves further.

In addition, in the clip disclosed here, since the container and the lid member can be fixed by reliably bringing into close contact with each other, a problem that the lid member comes off the container during transportation can be prevented. In particular, in a case where the accommodated object is a laminate of sheet-like or sheet-shaped cell cultures, it is possible to transport the device with the inside of the container reliably brought into a liquid-tight state, the laminate can be prevented from shifting or breaking as bubbles enter and move in the container, and the laminate can be preserved over the long term while maintaining a shape thereof and preventing deformation.

Without being limited to the details of the disclosed embodiments, those skilled in the art can realize or implement clips that have different configurations and shapes by suitably combining configurations or features of each of the clips according to the embodiments shown in FIGS. 4-6 and a shape thereof. For example, the cover member 9 or the cover member 9A may be combined with the base member 8, the base member 8A, or the base member 8B. The ridge portion 85, the ridge portion 85B, the protruding wall 86, or the protruding wall 86B may be combined with the base member 8, the base member 8A, or the base member 8B.

The detailed description above describes embodiments of a container and a clip, and methods of use, representing examples of the inventive container, clip and methods of use disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A device for holding a fragile object in liquid to prevent damage to the fragile object, the device comprising:
    a container with a closed bottom and an open top, the container comprising a bottom wall defining the closed bottom of the container, the container also comprising an annular side wall extending upwardly away from the bottom wall and surrounding a space to accommodate the liquid and the fragile object, the annular side wall terminating at an upper end, the annular side wall possessing an inner periphery defining an inner diameter of the annular side wall;
    a lid configured to close the open top of the container and seal the container when the liquid fills the space in the container and the fragile object is in the liquid so that the space is a liquid-tight space;
    a plate-shaped protecting member positionable, when the lid closes the open top of the container while the liquid fills the space and the fragile object is in the liquid, between the lid and a top surface of the liquid so the plate-shaped protecting member contacts the top surface of the liquid and the lid is spaced from the liquid;
    the plate-shaped protecting member possessing an outer periphery defining an outer diameter of the protecting member, the outer diameter of the plate-shaped protecting member being greater than the inner diameter of the annular side wall so that when the plate-shaped protecting member is positioned between the lid and the top surface of the liquid and is in contact with the top surface of the liquid, the outer periphery of the plate-shaped protecting member extends outwardly beyond the inner periphery of the annular side wall, and the plate-shaped protecting member extends across an entirety of the upper end of the annular side wall and covers the liquid in the space;
    the lid being separate from the plate-shaped protecting member so that upon removing the lid from the container the lid separates from the plate-shaped protecting member and does not cause ripples in the liquid that might otherwise damage the fragile object in the liquid; and
    the plate-shaped protecting member being separate from the container so that after removing the lid from the container the plate-shaped protecting member is separable from the container and is movable away from the liquid in the space to expose the liquid.

2. The device according to claim 1, wherein the plate-shaped protecting member includes a surface that contacts the top surface of the liquid, the surface of the plate-shaped protecting member being a water-repellent treated surface.

3. The device according to claim 1, wherein the plate-shaped protecting member is fluid impermeable.

4. The device according to claim 1, wherein the lid and the container each include threaded portions configured to threadedly engage one another to produce the liquid-tight space.

5. The device according to claim 1, wherein the container includes an annular rim extending upwardly from the bottom wall and spaced radially outwardly of the annular side wall so that an annular gap exists between the annular rim and the annular side wall.

6. The device according to claim 5, wherein the annular rim possesses an outer diameter, the outer diameter of the plate-shaped protecting member being less than the outer diameter of the annular rim.

7. The device according to claim 1, wherein the lid includes a plate-shaped top and a skirt wall extending downwardly from the plate-shaped top, the skirt wall possessing an inner diameter, an outer diameter of the plate-shaped protecting member being less than the inner diameter of the skirt wall.

8. The device according to claim 1, wherein the container includes an upper portion and a lower portion, the lower portion of the container being positioned between the bottom wall of the container and the upper portion of the container, the annular side wall constituting the lower portion of the container, the upper portion of the container being between the open top of the container and the lower portion of the container, the upper portion of the container possessing an inner diameter, the inner diameter of the upper portion of the container being greater than the inner diameter of the annular side wall of the container.

9. The device according to claim 8, wherein the outer diameter of the plate-shaped protecting member is less than the inner diameter of the upper portion of the container.

10. The device according to claim 8, wherein the lid includes a plate-shaped top and a skirt wall projecting away from the plate-shaped top, the skirt wall including a first threaded portion configured to threadedly engage a second threaded portion on the container to close and seal the container, the lid also including a projection portion integral with the plate-shaped top and protruding away from the plate-shaped top, the projection portion contacting the plate-shaped protecting member when the first threaded portion on the skirt wall of the lid threadedly engages the second threaded portion on the container to close and seal the container.

11. A device for holding liquid and a fragile object in the liquid to prevent damage to the fragile object, the device comprising:
a container for accommodating the fragile object and the liquid, the container including a bottom wall, an upstanding side wall extending upwardly away from the bottom wall and an open end, the upstanding side wall possessing an inner periphery surrounding a space, the upstanding side wall terminating at an upper end;
a lid engageable with the container for sealing the container when the liquid and the fragile object are accommodated in the space in the container, and disengageable from the container to allow the fragile object to be removed from the space;
a protecting member configured to be positioned between a top surface of the liquid in the space and the lid, the protecting member possessing an outer periphery, the outer periphery of the protecting member being configured relative to the inner periphery of the upstanding side wall so that when the protecting member is positioned between the lid and the top surface of the liquid and is in contact with the top surface of the liquid, the outer periphery of the protecting member extends outwardly beyond the inner periphery of the upstanding side wall and the protecting member extends across an entirety of the upper end of the side wall and covers the liquid in the space;
the protecting member being separate from the lid so that upon disengaging the lid from the container, the lid moves relative to the protecting member while the protecting member remains in contact with the top surface of the liquid in the space; and
the protecting member being separate from the container so that after disengaging the lid from the container the protecting member is separable from the container and is movable away from the liquid in the space to expose the liquid; and
the device being configured to form a liquid-tight space in the container by covering a surface of the liquid in the container with the protecting member and further covering the protecting member and the open end of the container with the lid member.

12. The device according to claim 11, wherein at least one of the protecting member and the lid member includes a surface that is water-repellent treated.

13. The device according to claim 11, wherein the protecting member is flexible.

14. The device according to claim 11, wherein the protecting member is fluid-impermeable.

15. The device according to claim 11, wherein the lid includes a plate-shaped top and a skirt wall extending downwardly from the plate-shaped top, the skirt wall possessing an inner diameter, the protecting member being a plate-shaped protecting member that possesses an outer diameter less than the inner diameter of the skirt wall.

16. The device according to claim 11, wherein the container includes an upstanding annular rim extending upwardly away from the bottom wall, the side wall being spaced radially inwardly from the annular rim so that an annular gap exists between the annular rim and the side wall.

17. The device according to claim 16, wherein the side wall possesses an outer diameter and the annular rim possesses an outer diameter, the protecting member being a plate-shaped protecting member that possesses an outer diameter greater than the outer diameter of the side wall and less than the outer diameter of the annular rim.

18. The device according to claim 11, wherein the container includes an upper portion and a lower portion, the lower portion of the container being positioned between the bottom wall of the container and the upper portion of the container, the side wall constituting the lower portion of the container, the upper portion of the container being between the open top of the container and the lower portion of the container, the side wall of the container possessing an inner diameter, the upper portion of the container possessing an inner diameter, the inner diameter of the upper portion of the container being greater than the inner diameter of the side wall of the container, the protecting member being a plate-shaped protecting member that possesses an outer diameter greater than the inner diameter of the side wall of the container and less than the inner diameter of the upper portion of the container.

19. A clip in combination with a device for holding liquid and a fragile object in the liquid to prevent damage to the fragile object, the device for holding liquid and the fragile object in the liquid to prevent damage to the fragile object comprising:
a container for accommodating the fragile object and the liquid, the container including a bottom wall, an upstanding side wall extending upwardly away from the bottom wall and an open end, the upstanding side wall possessing an inner periphery surrounding a space, the upstanding side wall terminating at an upper end;
a lid engageable with the container for sealing the container when the liquid and the fragile object are accommodated in the space in the container, and disengageable from the container to allow the fragile object to be removed from the space;
a protecting member configured to be positioned between a top surface of the liquid in the space and the lid, the protecting member possessing an outer periphery, the outer periphery of the protecting member being configured relative to inner periphery of the upstanding side wall so that when the protecting member is positioned between the lid and the top surface of the liquid and is in contact with the top surface of the liquid, the outer periphery of the protecting member extends outwardly beyond the inner periphery of the upstanding side wall and the protecting member extends across an entirety of the upper end of the side wall and covers the liquid in the space;
the protecting member being separate from the container so that upon disengaging the lid from the container, the lid moves relative to the protecting member while the protecting member remains in contact with the top surface of the liquid in the space;
the protecting member being separate from the container so that after disengaging the lid from the container, the protecting member is separable from the container and is movable away from the liquid in the space to expose the liquid; and
the device being configured to form a liquid-tight space in the container by covering a surface of the liquid in the container with the protecting member and further covering the protecting member and the open end of the container with the lid member; and the clip comprising:
a cover member and a base member which are configured to press and sandwich, from above and below, the device for holding liquid and the fragile object in the liquid to prevent damage to the fragile object.

20. A method of protecting a fragile object in a liquid comprising:
positioning the fragile object and the liquid in a space in a container, the container including an open top and a bottom wall defining a closed bottom of the container, the container also including an upstanding side wall that extends away from the bottom wall and terminates at an upper end, the upstanding side wall possessing an inner periphery that faces towards and surrounds the space, the liquid contacting the inner periphery of the upstanding side wall and filling the space in the container from the closed bottom to the upper end of the upstanding side wall so that a top surface of the liquid is exposed;
moving a protecting member relative to the container and positioning a first surface of the protecting member in direct contact with the top surface of the liquid that is exposed, the protecting member possessing a second surface facing in a direction opposite the first surface, the protecting member possessing an outer periphery, the positioning of the first surface of the protecting member in direct contact with the top surface of the liquid including positioning the protecting member relative to the upstanding side wall such that the outer periphery of the protecting member is positioned outwardly of the inner periphery of the upstanding side wall while the protecting member is in direct contact with the top surface of the liquid;
moving a lid relative to both the container and the protecting member and toward the second surface of the protecting member; and
covering the container with the lid while a portion of the lid contacts the second surface of the protecting member so that the space is a liquid-tight space, and the covering of the container with the lid occurring after the protecting member is positioned in direct contact with the top surface of the liquid that is exposed and after the outer periphery of the protecting member is positioned outwardly of the inner periphery of the upstanding side wall.

21. The method according to claim 20, wherein the top surface of the liquid is positioned above the top end of the upstanding side wall as the protecting member is brought into direct contact with the top surface of the liquid.

* * * * *